US00PP24999P2

(12) United States Plant Patent
Horvath

(10) Patent No.: US PP24,999 P2
(45) Date of Patent: Oct. 21, 2014

(54) ***ANDROPOGON GERARDII* PLANT NAMED 'INDIAN WARRIOR'**

(50) Latin Name: *Andropogon gerardii*
Varietal Denomination: Indian Warrior

(71) Applicant: Brent Horvath, Fontana, WI (US)

(72) Inventor: Brent Horvath, Fontana, WI (US)

( * ) Notice: Subject to any disclaimer, the term of this patent is extended or adjusted under 35 U.S.C. 154(b) by 0 days.

(21) Appl. No.: 13/815,046

(22) Filed: Jan. 28, 2013

(51) Int. Cl.
*A01H 5/00* (2006.01)

(52) U.S. Cl.
USPC ..... Plt./384

(58) Field of Classification Search
USPC ..... Plt./384
See application file for complete search history.

*Primary Examiner* — Annette Para

(57) ABSTRACT

A new, distinct *Andropogon gerardii* plant as shown and described, characterized by darker green colored foliage, uniform red fall color and a height of 150-180 cm.

1 Drawing Sheet

Latin name: *Andropogon gerardii.*
Cultivar name: 'Indian Warrior'.

BACKGROUND OF THE INVENTION

The present invention relates to a new form of *Andropogon gerardii* plant named 'Indian Warrior'. 'Indian Warrior' is a seedling of an *Andropogon gerardii* selection, not patented, characterized by darker green colored foliage, uniform red fall color and a height of 150-180 cm, compared to lighter green foliage, buff to orange fall color, and the taller habit of 180-210 cm of the parent plant. The new plant was grown as a seedling by the inventor in the ground as a stock block of *Andropogon gerardii* seedlings at a wholesale perennial nursery in Hebron, Ill. in 2005. The selection of this plant was due to its shorter habit and darker green foliage and uniform red fall color. Asexual, vegetative division propagation has been the only means of reproduction. Propagation has taken place at Hebron, Ill. since 2006. In 2009 we planted 60 plants in 1 gallon pots. To date these plants have remained uniform in height, and foliage color. The new *Andropogon gerardii* has shown to be stable and identical in reproduction to the parent after making over 650 vegetative divisions from 2006 to 2011.

SUMMARY OF THE INVENTION

In the following description, color references are made to The Royal Horticultural Society Colour Chart (copyright 2001). The new *Andropogon gerardii* plant named 'Indian Warrior' has shown the characteristisc of a 150-180 cm height and darker green foliage and uniform red fall color to be unique and stable. For purpose of the comparison the new plant will be referred to as 'Indian Warrior'.

Plants of 'Indian Warrior' can be compared to plants of *Andropogon gerardii* the species. 1. 'Indian Warrior' has a height in the range of 150-180 cm compared to the height of *Andropogon gerardii* which has an average height of 210 cm. 2. 'Indian Warrior' has a foliage color of RHS 137A coloring to N77 compared to *Andropogon gerardii* which has a foliage color of RHS136C coloring to buff to orange.

Plants of 'Indian Warrior' can be compared to plants of *Andropogon gerardii* 'Red Bull' not patented. 1. The 'Indian Warrior' has a height in the range of 150-180 cm compared to the height of *Andropogon gerardii* 'Red Bull' which has an average height of 180-210 cm. 2. The new *Andropogon* has a foliage color of RHS 137A compared to *Andropogon gerardii* 'Red Bull' which has foliage color that is lighter green, close to RHS 136C. 3. 'Indian Warrior' has a uniform red fall color RHS N77 and is propagated by division while the *Andropogon gerardii* 'Red Bull' has a variable orange red fall color and is propagated by seed.

DESCRIPTION OF PHOTOGRAPHS

Figure 1:
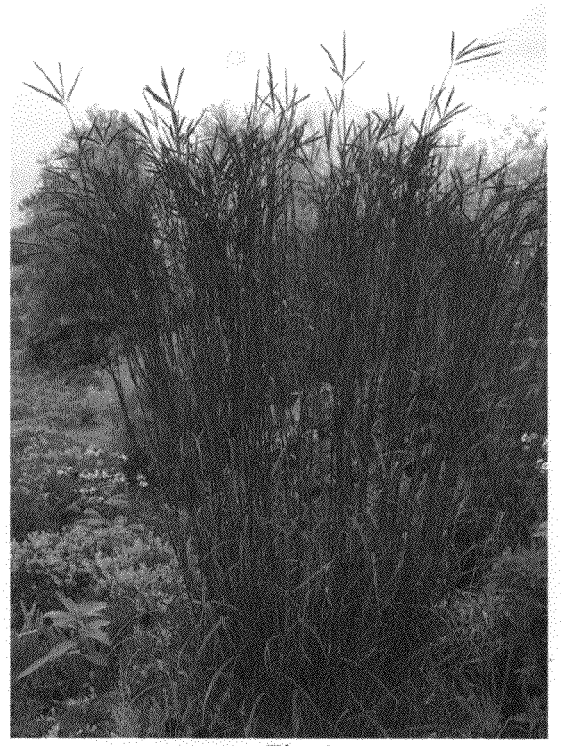

FIG. 1. Shows a plant in the ground with fall color in September.

Figure 2:
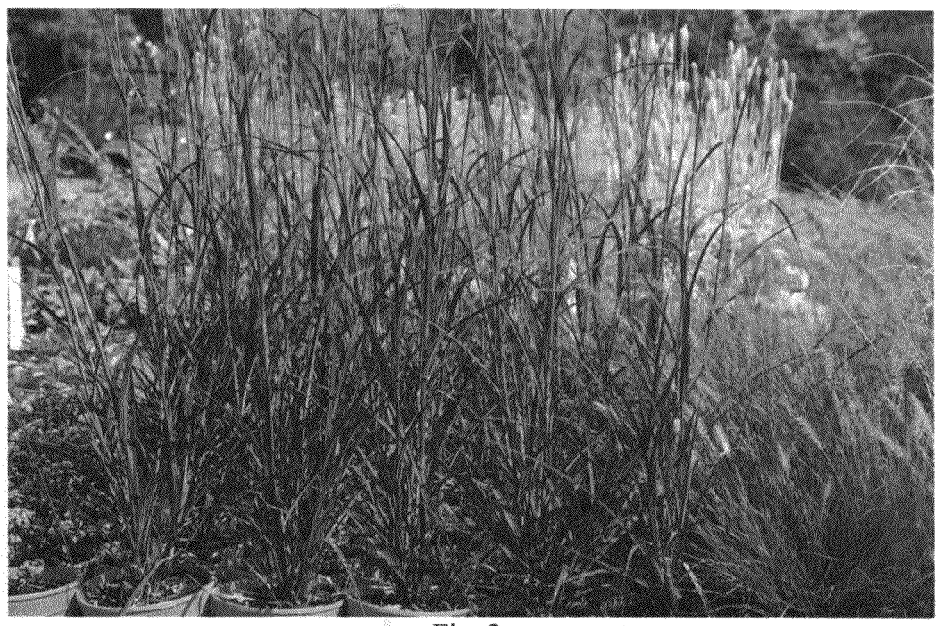

FIG. 2. Shows a plant in pots with fall foliage color in September.

DETAILED BOTANICAL DESCRIPTION

In the following description, color references are made to The Royal Horticultural Society Colour Chart. The plant herein described is an established 5 year old plant growing in a garden, grown in full sun and irrigated in Hebron, Ill. USA. Measurements and numerical values represent averages of typical plants.

Botanical classification: *Andropogon gerardii* cultivar 'Indian Warrior'.

Parentage: *Andropogon gerardii* seedling.

Propagation: Vegetative division.

Plant description: Overall habit of the new *Andropogon* is clumping with upright culms topped by red colored flowers beginning in August. Vigor is moderate.

*Plant height.*—150-180 cm.

*Plant width.*—60-70 cm.

Foliage and stems:

*Foliage description.*—Glabrous, flat blade, sheathed from node of attachment to ligule, linear.

*Type.*—Deciduous, grass growing in culms.

*Shape.*—Blade.

*Sheath.*—1 cm wide, 12 cm long, surface — glabrous.

*Ligules.*—Up to 2 mm long and less than 4 mm wide.

*Number of blades.*—Typically 3 to 4 blades per stem.

*Blade length.*—1 cm wide, 41 cm long with out the sheath.

*Sheath.*—1 cm wide, ranging from 7 to 17 cm long.

*Adaxial leaf description.*—The leaf color is green color 137 A coloring up to N77.

*Abaxial leaf description.*—The leaf color is green color 137 B coloring up to N77.

*Veins.*—Parallel, same color as surrounding leaf on both top and bottom of leaf.

*Culm description.*—Erect, cylindrical, typically with 3 or 4 leaves.

*Culm or stem diameter.*—5 mm average, but typically 3-4 mm between the nodes and swelling to 8 mm at the base of the internodes.

*Number of culms or stems per clump.*—Over 100.

*Node description.*—Cylindrical.

*Number of nodes per culm.*—Average 7.

*Length of internodes.*—Ranges from 10-20 cm.

Flower inflorescence:

*Inflorescence type.*—Terminal raceme with sessile and pedicillate spikelets.

*Rachis.*—2 mm wide and up to 60 cm long, color starts 137 A coloring up to N77.

*Overall raceme size.*—10 cm wide, 12 cm long.

*Rames.*—4, 2 mm wide, 7-20 cm long.

*Inflorescence color.*—As a whole the color is N77.

*Spikelet.*—Sessile and pedicellate — both 4-12 mm long, color is N77.

*Rachilla.*—Less than 1 mm wide, 5 mm long, color starts 137 A coloring up to N77.

*Individual floret size.*—1 mm wide, 30 mm long including awn.

*Lower glume.*—1 mm wide, 7 mm long, color starts 137 A coloring up to N77.

*Lemma.*—Outer and inner — both, 1 mm wide, 7 mm long, color starts 137 A coloring up to N77.

*Awn size.*—Less than 1 mm wide and average 10 mm long.

*Pedicels.*—4 to 5 per, rames and are shorter toward the base of the plant.

*Flower number.*—Approximately 15 florets per rames, average 60 per spikelet, mature spikelet measuring 5 cm wide, 10 cm long.

Cynocium:

*Stigma.*—2. color close to N77.

Androecium:

*Anthers.*—Number 3, color — is orange.

*Anther size.*—2-4 mm long by 1 mm wide.

*Fertility.*—Fertile with 3 Anthers and 3 Stamens.

*Blooming habit.*—Terminal raceme on up to 150-180 cm stems.

*Bloom period and duration.*—Last two weeks of August to the end of September.

*Bloom color.*—Close to N77.

*Fruit or seeds.*—Color is close to N77, size is 1 mm wide, 7 mm long.

*Scent.*—No scent.

*Roots.*—Stiff, fibrous, and freely branching.

*Fruit.*—Seed identical to the species except color is more red, close to N77.

Hardiness: United States Department of Agriculture Zones 4-9.

Disease resistance: Plants are not susceptible to any major pests or diseases. Regarding, *Andropogon gerardii* plant named 'Indian Warrior'.

I claim:

1. A new, distinct *Andropogon gerardii* plant as shown and described, characterized by darker green colored foliage, uniform red fall color and a height of 150-180 cm.

* * * * *